*(12)* United States Patent
Jugl et al.

(10) Patent No.: US 9,192,716 B2
(45) Date of Patent: Nov. 24, 2015

(54) DRIVE MECHANISM FOR A DRUG DELIVERY DEVICE AND DRUG DELIVERY DEVICE

(75) Inventors: Michael Jugl, Frankfurt am Main (DE); Torsten Kraft, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/002,176

(22) PCT Filed: Mar. 15, 2012

(86) PCT No.: PCT/EP2012/054560
§ 371 (c)(1),
(2), (4) Date: Aug. 29, 2013

(87) PCT Pub. No.: WO2012/123543
PCT Pub. Date: Sep. 20, 2012

(65) Prior Publication Data
US 2013/0338590 A1 Dec. 19, 2013

(30) Foreign Application Priority Data

Mar. 16, 2011 (EP) .................................. 11158491

(51) Int. Cl.
*A61M 37/00* (2006.01)
*A61M 5/145* (2006.01)
*A61M 5/315* (2006.01)

(52) U.S. Cl.
CPC ......... *A61M 5/1452* (2013.01); *A61M 5/31511* (2013.01); *A61M 5/14546* (2013.01); *A61M 2005/31518* (2013.01)

(58) Field of Classification Search
CPC ......... A61M 5/178; A61M 5/20; A61M 5/24; A61M 5/315; A61M 5/31511; A61M 5/31578; A61M 5/14; A61M 5/142; A61M 5/14236; A61M 5/1424; A61M 5/14244; A61M 5/145; A61M 5/1452; A61M 5/14546; A61M 2005/14506; A61M 2005/14533; A61M 2005/31518; A61M 5/1454; F16H 25/2409; F16H 29/20; F16H 55/26; F16H 55/303
USPC ......... 604/131, 137, 151, 154, 155, 221, 224, 604/207
See application file for complete search history.

(56) References Cited

U.S. PATENT DOCUMENTS 3,985,037 A * 10/1976 Peyser ........................... 474/154
4,300,554 A * 11/1981 Hessberg et al. ............. 604/135
(Continued)

FOREIGN PATENT DOCUMENTS

| DK | WO 01/72360 A1 * | 10/2001 | ............ A61M 5/315 |
|---|---|---|---|
| DK | WO 01/78812 A1 * | 10/2001 | ............ A61M 5/315 |
| EP | 1372768 | 8/2008 | |

(Continued)

OTHER PUBLICATIONS
International Search Report for Int. App. No. PCT/EP2012/054560, completed Jun. 5, 2012.

*Primary Examiner* — Edelmira Bosques
*Assistant Examiner* — Nicholas Meghri
(74) *Attorney, Agent, or Firm* — McDonnell Boehnen Hulbert & Berghoff LLP

(57) ABSTRACT

The drive mechanism is suitable for a permanent delivery of a drug from a compact drug delivery device, which may be carried on the body. The drive mechanism comprises a flexible advance cable bearing a coupling feature of longitudinal extension. The advance cable is guided by a guide means. A drive means engages the coupling feature and thus enables an advancement of the advance cable according to the guide means. An end piece is provided to push a plug or bung of a cartridge containing a drug, and the end piece is driven by the advance cable. The drive means is permanently engaged with the coupling feature. This allows a permanent advancement of the plug or bung by means of the drive mechanism.

8 Claims, 2 Drawing Sheets

(56) References Cited

U.S. PATENT DOCUMENTS

| | | | | |
|---|---|---|---|---|
| 5,261,882 A | * | 11/1993 | Sealfon | 604/135 |
| 5,599,314 A | * | 2/1997 | Neill | 604/207 |
| 2005/0251097 A1 | * | 11/2005 | Mernoe | 604/221 |
| 2006/0264889 A1 | * | 11/2006 | Moberg et al. | 604/500 |

FOREIGN PATENT DOCUMENTS

| | | |
|---|---|---|
| WO | 01/72360 | 10/2001 |
| WO | 01/78812 | 10/2001 |
| WO | 02/076535 | 10/2002 |
| WO | 02/076538 | 10/2002 |

* cited by examiner

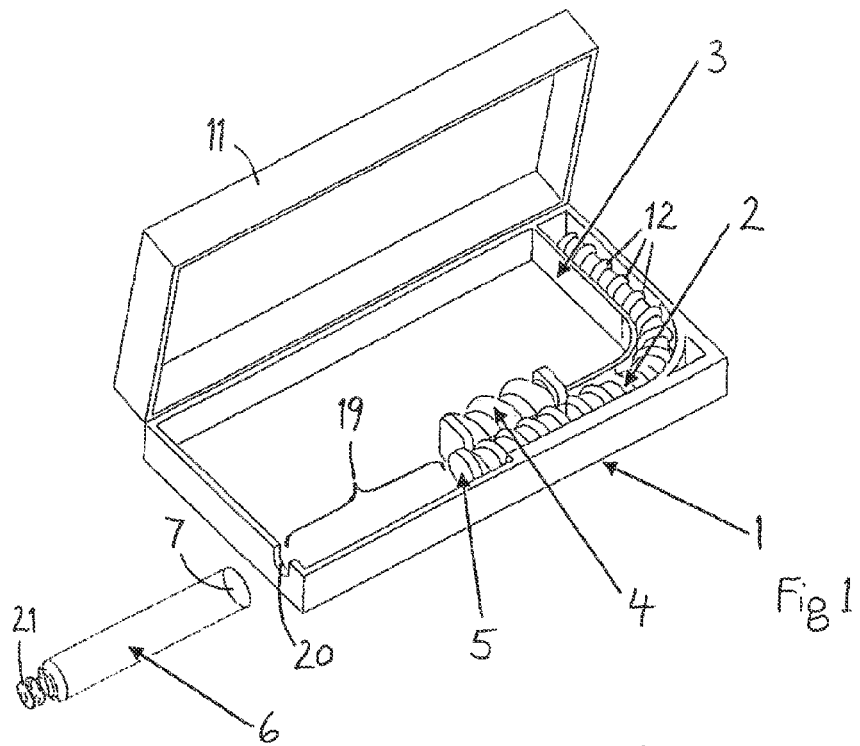
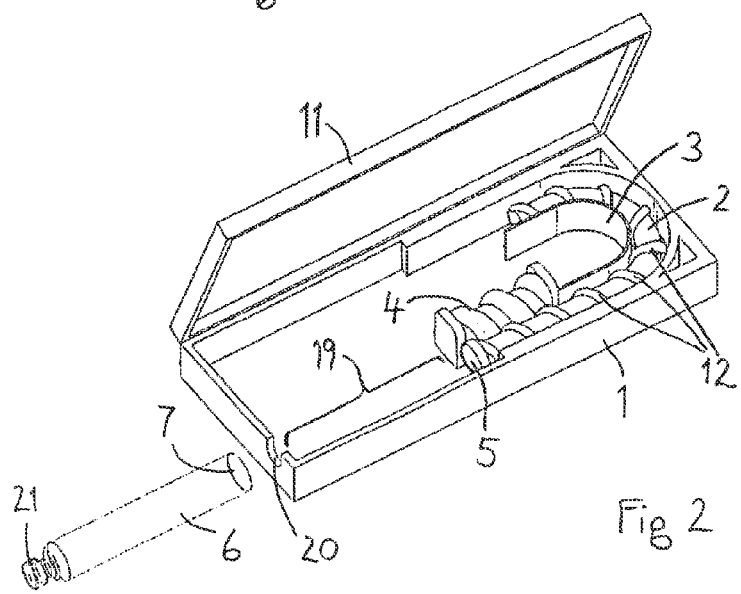

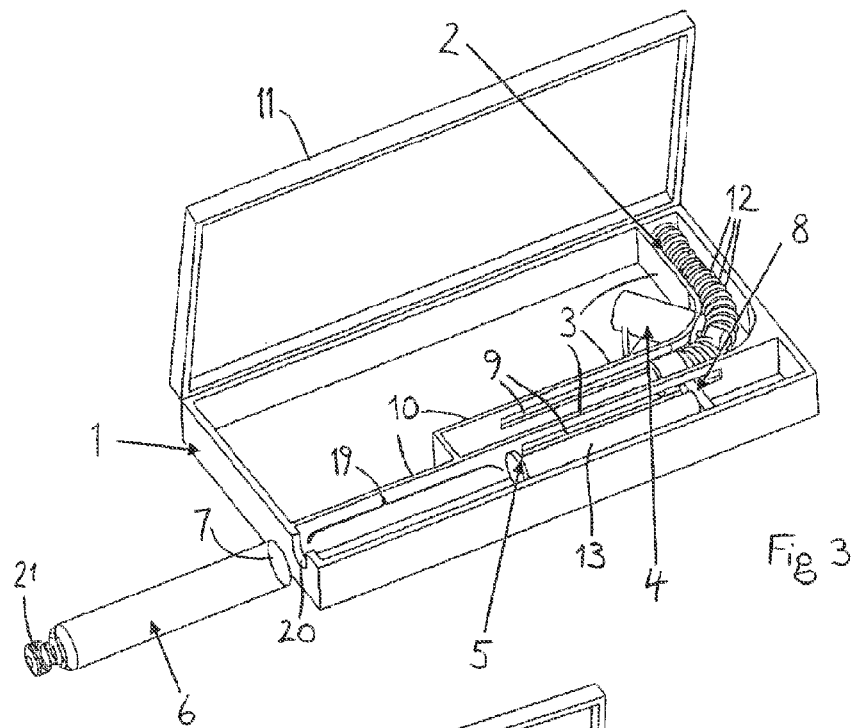
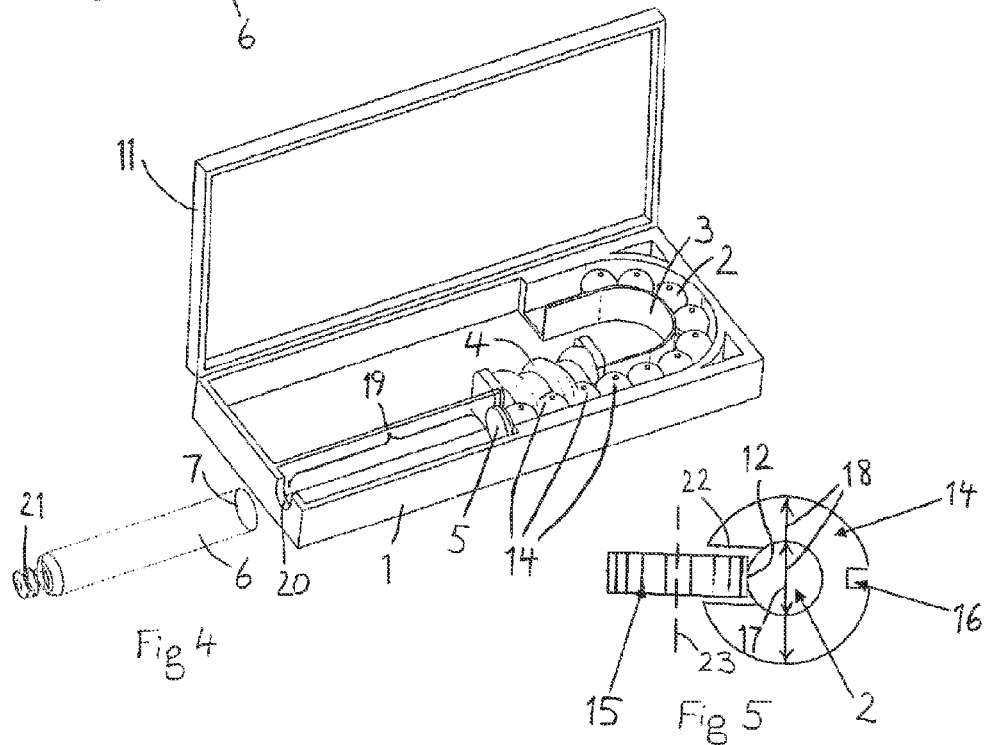

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2012/054560 filed Mar. 15, 2012, which claims priority to European Patent Application No. 11158491.8 filed Mar. 16, 2011. The entire disclosure contents of these applications are herewith incorporated by reference into the present application.

FIELD OF DISCLOSURE

The present invention relates to a drive mechanism for a drug delivery device and to a drug delivery device that is provided with such a drive mechanism.

BACKGROUND

EP 1 372 768 B1 describes a drive mechanism for an injection device in which a semi-rigid belt with a track is used to drive a piston member. A belt drive means is provided to drive the belt a preselected way. It comprises a tooth for a selective engagement with the track and allows an advancement of the belt only in one direction.

SUMMARY

It is an object of the present invention to provide a new drive mechanism and a drug delivery device of compact dimensions.

This object is achieved with a drive mechanism and a drug delivery device according to the appended claims. Further objects are achieved with embodiments according to the dependent claims.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The housing of the drug delivery device can be an exterior housing or some kind of an insert connected with an exterior housing. The housing may enable the safe, correct, and/or easy handling of the device and/or may be provided to protect the device from harmful liquids, dust or dirt. The housing can be unitary or a multipart component and may house a cartridge, from which doses of a drug can be dispensed. The housing may be provided with a lid, so that it can be opened to insert a cartridge containing a drug. The drive mechanism can be used to expel a drug from a cartridge that is inserted in the housing. The drug delivery device can be a disposable or re-usable device. The drug may be administered by a needle, or the device may be needle-free.

The drive mechanism comprises a flexible advance cable bearing a coupling feature of longitudinal extension. The advance cable is guided by a guide means. A drive means engages the coupling feature and thus enables an advancement of the advance cable according to the guide means. An end piece is provided to push a plug or bung of a cartridge containing a drug, and the end piece is driven by the advance cable. The drive means is provided for a permanent engagement with the coupling feature. This allows a permanent advancement of the plug or bung by means of the drive mechanism.

In an embodiment of the drive mechanism, the advance cable has an outer diameter that corresponds to an inner diameter of the cartridge.

In a further embodiment of the drive mechanism, the advance cable is provided with beads or balls having an outer diameter that exceeds the outer diameter of the advance cable and corresponds to the inner diameter of the cartridge.

In a further embodiment of the drive mechanism, the advance cable is a plastics material, and the beads or balls are formed as integral parts of the advance cable.

In a further embodiment of the drive mechanism, the beads or balls are separate parts arranged according to the guide means, and the advance cable passes through the beads or balls.

In a further embodiment of the drive mechanism, the drive means is a worm or pinion, and the coupling feature is a screw thread.

In a further embodiment of the drive mechanism, the drive means is a worm or pinion, and the coupling feature is a sequence of annular protrusions.

In a further embodiment of the drive mechanism, the drive means is a worm or pinion, and the coupling feature is a rack.

In a further embodiment of the drive mechanism, the advance cable is a plastics material, and the end piece is formed as an integral part of the advance cable.

In a further embodiment of the drive mechanism, the end piece is applied to the advance cable as a separate part formed from a metal.

In a further embodiment of the drive mechanism, a piston rod is driven by the advance cable, and the end piece is provided on the piston rod.

In a further embodiment of the drive mechanism, the piston rod is driven parallel to the advance cable.

The drive mechanism is particularly suitable for a permanent delivery of a drug from a compact drug delivery device, which may be carried on the body.

The drug delivery device comprises a housing and a flexible advance cable bearing a coupling feature of longitudinal extension, which is arranged inside the housing. A guide means, which guides the advance cable, is formed inside the housing. A drive means engages the coupling feature and thus enables an advancement of the advance cable according to the guide means. An end piece is provided to push a plug or bung of a cartridge containing a drug and is driven by the advance cable. The drive means is provided for a permanent engagement with the coupling feature.

In an embodiment of the drug delivery device, the end piece is applied to the advance cable.

In a further embodiment of the drug delivery device, the end piece is located on a piston rod, and the piston rod is advanced by the advance cable.

The length of the advance cable may exceed the dimensions of the housing, and the advance cable may be bent to fit into the housing. This allows particularly compact dimensions of the drug delivery device.

In the following, examples and embodiments of the drive mechanism and the drug delivery device are described in detail in conjunction with the appended figures.

BRIEF DESCRIPTION OF THE FIGURES

FIG. 1 shows a simplified perspective view of an opened drug delivery device comprising an embodiment of the drive mechanism.

FIG. 2 shows a cross-section according to FIG. 1 of a further embodiment.

FIG. 3 shows a cross-section according to FIG. 1 of a further embodiment.

FIG. 4 shows a cross-section according to FIG. 1 of a further embodiment.

FIG. 5 shows a detail of the embodiment of FIG. 4.

DETAILED DESCRIPTION

FIG. 1 shows a perspective view of an embodiment of the drug delivery device in an opened state. A housing 1 contains a drive mechanism comprising a flexible advance cable 2, which may be bent as shown in the figure. A guide means 3, which may be formed by sidewalls, for instance, is provided inside the housing 1 to guide the advance cable 2 along a prescribed way within the housing 1 and to inhibit a lateral deviation of the advance cable 2. Thus the advance cable 2 may be stored in a compact volume and operated as a driving agent.

A drive means 4 is also arranged in the housing 1 and is engaged with a coupling feature 12 on the surface of the advance cable 2. The coupling feature 12 extends along a major portion of the longitudinal extension of the advance cable 2 in order to facilitate a permanent advancement of the advance cable 2 by means of the coupling feature 12. The drive means 4 is represented in FIG. 1 as a worm, and the coupling feature 12 is shown to be a screw thread, the worm and the screw thread forming a worm drive. Instead, the drive means 4 may be a pinion, a quill drive, or a similar device. Instead of a continuous screw thread, the coupling feature 12 may comprises a sequence of separate annular protrusions. The position of the drive means 4 may differ from the location shown in FIG. 1. The drive means 4 may be operated by a loaded spring or by an electric motor supplied with a battery, for example. These components, which are known per se, can be applied as desired according to individual requirements and are not represented in the figures.

The housing 1 can be opened, and a cartridge 6 containing a drug may then be inserted into an empty space 19 left in the housing 1 for this purpose. In the embodiment shown in FIG. 1 the housing 1 comprises a lid 11, which may be hinged and can be opened. FIG. 1 shows the cartridge 6 outside the housing 1, and the direction in which the cartridge 6 is arranged when properly inserted is indicated. An end piece 5 of the advance cable 2 is provided to push a plug 7 or bung of the cartridge 6.

When the cartridge 6 is inserted and the drive mechanism is actuated, the advance cable 2 is being advanced and the end piece 5 is maintained in contact with the plug 7 or bung, which is consequently also permanently advanced. An outlet 21 at the other end of the cartridge 6 is arranged in or at an opening 20 of the housing 1, so that the drug is being expelled from the cartridge 6 and may be injected, by means of a needle, for instance, into a patient's body.

The end piece 5 may be an integral part of the advance cable 2, particularly if the advance cable 2 is moulded from a plastics material as one part including the end piece 5. Instead, the end piece 5 may be formed from a metal, like steel, aluminum, brass or other, and may be arranged as a separate part between the advance cable 2 and the plug 7 or bung, or may be fastened to the advance cable 2 by pressing, hammering, forging, clipping or the like.

The outer diameter of the advance cable 2 preferably corresponds to the inner diameter of the cartridge 6, at least approximately. The guide means 3 allows the drive means 4 to exert a longitudinal force on the advance cable 2, without causing a lateral deviation of the flexible advance cable 2 from the intended longitudinal path.

FIG. 2 shows another embodiment, in which the radius of curvature of the bent portion of the advance cable 2 is smaller, so that the arrangement is more compact than in the embodiment according to FIG. 1. The pitch of the screw thread may be adapted to provide the required flexibility of the advance cable 2. In FIGS. 1 and 2 similar elements and corresponding components are designated with the same reference numerals.

FIG. 3 shows still another embodiment, in which the position of the drive means 4 is changed, the screw thread of the coupling feature 12 has a smaller pitch, and the end piece 5 is not directly applied to and in contact with the advance cable 2. The end piece 5 is instead provided on a piston rod 13, which is shifted within a compartment that is formed by an inner sidewall 10 of the housing 1. The piston rod 13 is advanced by means of a transverse bar 8 protruding from the advance cable 2. The guide means 3 guides a portion of the advance cable 2 parallel to the movement of the piston rod 13. The advance cable 2 may be prevented from a rotation around its longitudinal axis by threads or spikes which may be formed on the surface of the advance cable 2 and may be guided in tracks 9 provided in the sidewalls 10 of the guide means 3. The bar 8, which may be formed resembling a sprig or cantilever, for example, passes through an opening formed by one of the tracks 9 and extends far enough to be able to push the piston rod 13 in the direction of the cartridge 6.

FIG. 4 shows another embodiment, in which the advance cable 2 is provided with beads 14 or balls having an outer diameter that exceeds the outer diameter of the advance cable 2 and preferably corresponds to the inner diameter of the cartridge 6. The beads 14 or balls allow the use of a thinner and therefore more flexible advance cable 2 and keep the advance cable 2 in its proper longitudinal direction with respect to the intended path of advancement. If the advance cable 2 is formed from a plastics material, the beads 14 or balls may be moulded together with the advance cable 2. Instead, the beads 14 or balls may be separate parts arranged in the compartment that is formed by the guide means 3, and the advance cable 2 may pass through openings or channels formed in the beads 14 or balls.

The beads 14 or balls may provide the coupling feature 12 which is engaged by the drive means 4. Instead, the beads 14 or balls may each comprise a recess formed in such a manner that the recesses uncover a longitudinal strip of the surface of the core of the advance cable 2. The coupling feature 12 may be provided by a toothing on said longitudinal strip, for example. The drive means 4 may comprise a worm as shown or a pinion fitting the rack that is formed by the toothing.

FIG. 5 shows a detailed view of a drive means 4 which is particularly suitable in conjunction with the beaded advance cable 2 of the embodiment according to FIG. 4. The drive means 4 comprises a pinion 15 engaging the coupling feature 12 on the core of the advance cable 2 within the recesses 22 of the beads 14 or balls. The axis 23 of rotation of the pinion 15 is orthogonal to the direction of longitudinal extension of the advance cable 2, which is the direction normal to the plane of the drawing. As can be seen from FIG. 5, the beads 14 or balls enlarge the outer diameter 17 of the advance cable 2 to the outer diameter 18 of the beads 14 or balls.

Grooves 16 may be formed in the beads 14 or balls as a means to prevent a rotation of the advance cable 2 around its longitudinal axis and to maintain the recesses 22 of the beads 14 or balls in the appropriate position with respect to the pinion 15 or other drive means 4. The grooves 16 may be guided by corresponding threads running along the guide means 3 or along the inner sidewalls 10 of the housing 1. The position and the realisation of the drive means 4 may vary and deviate from the examples shown in the figures.

The drive mechanism and the drug delivery device provided with the drive mechanism are especially useful for infusion devices like insulin pumps, which are used to inject the drug permanently.

Further, the drive mechanism and the drug delivery device provided with the drive mechanism may be used in an injection device, for example in an injection device for injecting insulin such as long or short acting insulin. Such an injection may take place once per day for long acting insulin, or several times a day, for example before or after a meal, for other types of insulin.

The invention claimed is:

1. A drive mechanism for a drug delivery device, comprising:
    a flexible advance cable bearing a coupling feature of longitudinal extension,
    a guide means guiding the advance cable,
    a drive means engaging the coupling feature and thus enabling an advancement of the advance cable according to the guide means, wherein the drive means is provided for a permanent engagement with the coupling feature and where the drive means is a worm or pinion, and the coupling feature is a screw thread, and
    an end piece, which is provided to push a plug or bung of a cartridge containing a drug and which is driven by the advance cable,
    the advance cable is provided with balls having an outer diameter that exceeds an outer diameter of the advance cable and corresponds to an inner diameter of the cartridge, and
    the end piece is pushed by a portion of the advance cable that enters the cartridge.

2. The drive mechanism according to claim 1, wherein the advance cable is a plastics material, and the balls are formed as integral parts of the advance cable.

3. The drive mechanism according to claim 1, wherein the balls are separate parts arranged according to the guide means, and the advance cable passes through balls.

4. The drive mechanism according to claim 1, wherein the advance cable is a plastics material, and the end piece is formed as an integral part of the advance cable.

5. The drive mechanism according to claim 1, wherein the end piece is applied to the advance cable as a separate part formed from a metal.

6. The drive mechanism according to claim 1, further comprising:
    a piston rod driven by the advance cable, which does not enter the cartridge, the end piece being provided on the piston rod, which enters the cartridge.

7. The drive mechanism according to claim 6, wherein the piston rod is driven parallel to the advance cable by means of a transverse bar protruding from the advance cable.

8. A drug delivery device, comprising:
    a housing, and
    a drive mechanism according to claim 1 arranged within the housing.

* * * * *